United States Patent [19]

Field et al.

[11] Patent Number: 5,283,336

[45] Date of Patent: Feb. 1, 1994

[54] METHOD FOR PREPARATION OF 7-HYDROXY-1,2,3,4-TETRAHYDROQUINOLINE FROM 1,2,3,4-TETRAHYDROQUINOLINE

[75] Inventors: George Field, Danville; Peter R. Hammond, Livermore, both of Calif.

[73] Assignee: The United States of America as represented by the United States Department of Energy, Washington, D.C.

[21] Appl. No.: 941,813

[22] Filed: Sep. 8, 1992

[51] Int. Cl.$^5$ .................................. C07D 215/20
[52] U.S. Cl. .................................. 546/179; 546/49; 546/178
[58] Field of Search ........................... 546/179

[56] References Cited

U.S. PATENT DOCUMENTS

| | | | |
|---|---|---|---|
| 3,015,661 | 1/1962 | Georgian | 546/15 |
| 3,162,675 | 12/1964 | Olah | 546/176 |
| 3,255,252 | 6/1966 | Gold | 546/143 |
| 3,379,730 | 4/1968 | Mathison | 546/150 |
| 3,459,755 | 8/1969 | Mathison et al. | 546/143 |
| 3,560,404 | 2/1971 | Jung et al. | 252/414 |
| 3,822,270 | 7/1974 | Reynolds . | |
| 3,860,599 | 1/1975 | Covelli | 546/179 |
| 3,932,415 | 1/1976 | Reynolds . | |
| 4,005,092 | 1/1977 | Reynolds . | |
| 4,622,400 | 10/1986 | Hammond | 546/179 |
| 4,945,176 | 7/1990 | Hammond et al. | 549/227 |

FOREIGN PATENT DOCUMENTS

| | | | |
|---|---|---|---|
| 55-40616 | 3/1980 | Japan . | |
| 301545 | 12/1928 | United Kingdom | 546/179 |

OTHER PUBLICATIONS

Hosztafi et al. Chem. Abstr. vol. 116 Entry 194668 f. (1991.).

Mayer, F., van Zutphen, L. and Phillips, H., "Eine neue Darstellungsweise von Hydrocarbostyril) und seinen Abkommlingen," Chrom. Des. 1927, 60, pp. 858–864.

Brown, H. C. and Heim, P., "Selective Reductions. XVIII. The Fast Reaction of Primary, Secondary, and Tertiary Amides with Diborane. A Simple, Convenient Procedure for the conversion of Amides to the Corresponding Amines," J. Org. Chem., vol. 38, No. 5 pp. 912–916 (1973).

Shigematsu, N., "Studies on the Synthetic Analgesics. XVI. Synthesis of 1-(2-tert-Aminoalkyl)-3,4-dihydrocarbostyrils," Diborane route, Chem. Pharm. Bull. (Tokyo) 1961, 9, pp. 970–975.

Sidhu, G. S., Thyagarajan, G. and Ansari, S., "Synthese von Carbonstyrilen und Dihydrocarbostyrilen," Liebigz Ann. Chem., pp. 218–224 (1959).

Primary Examiner—Donald G. Daus
Attorney, Agent, or Firm—Miguel A. Valdes; Roger S. Gaither; William R. Moser

[57] ABSTRACT

Methods for the efficient preparation of 7-hydroxy-1,2,3,4-tetrahydroquinoline include a first method in which the acylation of m-aminophenol obtains a lactam which is reduced to give the desired quinoline and a second method in which tetrahydroquinoline is nitrated and hydrogenated and then hydrolyzed to obtain the desire quinoline. 7-hydroxy-1,2,3,4-tetrahydroquinoline is used in the efficient synthesis of four lasing dyes of the rhodamine class.

3 Claims, No Drawings

METHOD FOR PREPARATION OF 7-HYDROXY-1,2,3,4-TETRAHYDROQUINOLINE FROM 1,2,3,4-TETRAHYDROQUINOLINE

The United States Government has rights in this invention pursuant to Contract No. W-7405-ENG-48 between the United States Department of Energy and the University of California for the operation of Lawrence Livermore National Laboratory.

TECHNICAL FIELD

The present invention relates to efficient methods for the preparation of 7-hydroxy-1,2,3,4-tetrahydroquinoline which is an intermediate useful in the economic manufacture of laser dyes.

BACKGROUND OF THE INVENTION

Large scale production of rhodamine class laser dyes depends upon the cost of the synthesis of these dyes. The high cost of intermediates can make large scale production of the laser dyes commercially impracticable.

SUMMARY OF THE INVENTION

The present invention provides for the efficient, cost-effective preparation of 7-hydroxy-1,2,3,4-tetrahydroquinoline which is an intermediate useful in the preparation of a class of dyes which lase at wavelengths between 540 and 570 nm.

The present invention further provides for the preparation of a class of laser dyes which exhibit lasing efficiency and photochemical stability for extended periods of operation from relatively inexpensive materials.

In general, the present invention is directed to efficient method for the preparation of the intermediate 7-hydroxy-1,2,3,4-tetrahydroquinoline, and to the use of this intermediate to prepare dyes of the general formula:

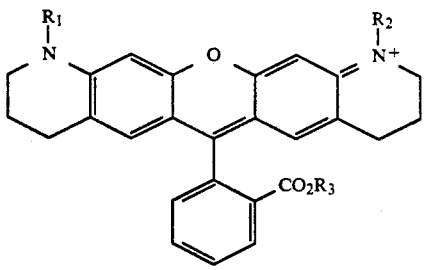

wherein $R_1$, $R_2$ and $R_3$ are each individually hydrogen or a linear alkyl or fluoroalkyl group of 1 to 10 carbon atoms.

These and other objects and advantages of the invention will be apparent in the description of the specific embodiments.

DETAILED DESCRIPTION OF THE INVENTION

I. Synthesis of 7-Hydroxy-1,2,3,4-Tetrahydroquinoline

A. m-Aminoohenol/Boron Hydride Method

Chart 1 shows the synthesis of 7-hydroxy-1,2,3,4-tetrahydroquinoline from m-amino phenol.

CHART 1

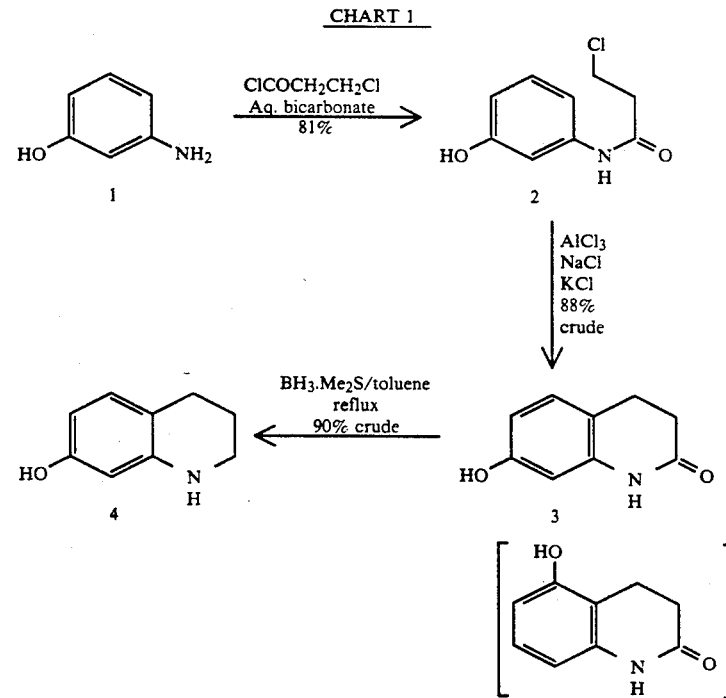

The acylation of m-aminophenol 1 to form the amide 2 can be performed in water with bicarbonate as base with little loss in yield and thereby avoiding expensive organic solvents.

The cyclization of the amide 2 to obtain the lactam 3 can be conducted in the presence of aluminum chloride, but this results in the formation of significant amounts of the undesired 5-hydroxy isomer. The use of a eutectic of aluminum chloride, sodium chloride and potassium chloride in the cyclization reaction reduces the formation of the undesired isomer, but leads to a noticeable exotherm and potential foaming.

The lactam group 3 is reduced to give the quinoline 4 with borane-methyl sulfide complex in toluene. The quinoline product 4 may be isolated as the maleate complex which is somewhat easier to crystallize than the free base.

EXAMPLE 1—3-Chloro-3'-hydroxypropionanilide

To a mixture of 21.82 g (0.2 mol) of m-aminophenol, 16.8 (0.2 mol) of sodium bicarbonate, 0.5 g of tetrabutylammonium hydrogen sulfate and 300 ml of water stirred under nitrogen and cooled in an ice bath to 4° C. was added dropwise 19.1 ml (25.4 g, 0.2 mol) of 3-choropropionyl chloride during 0.5 hour. The temperature held at 5° C. and the reaction mixture foamed. The slurry was stirred for a further 1.5 hr in the ice bath. The solid was collected, washed with water and dried to give 32 3 g (81%) of product as a white solid, melting point 132°–136.5° C.

EXAMPLE 2—7-Hydroxy-3,4-dihydrocarbostyril

A mixture of 10 g (50 mmol) of 3-chloro-3'-hydroxypropionanilide 2 and 26.67 g (200 mmol) of powdered aluminum chloride was put in an oil bath at 130° C. with a magnetic stirrer. The temperature was raised to 160° C. In about 10 min the reaction mixture liquified and foamed. The temperature was held at 145° to 160° C. Thin layer chromatography of the mixture at 1 hr 10 min showed there was no amide left. After 1 hr 40 min total of heating, 50 ml of water was cautiously added. Hydrogen chloride was given off and the reaction mixture boiled. Another 25 ml of water was added and the mixture stirred overnight. The precipitated product was collected and rinsed with water to give 7.35 g (90%) of off-white powder, melting point 217°–220° C. Recrystallization to isolate the desired isomer is needed.

EXAMPLE 3—7-Hydroxy-3,4-dihydrocarbostyril

A mixture of 20 g of potassium chloride, 20 g of sodium chloride and 160 g of aluminum chloride in a 500 ml flask with mechanical stirrer, condenser and thermometer was melted in an oil bath at 160° C. To it was added 40 g (0.2 mol) of 3-chloro-3'-hydroxy propionanilide 2 in portion during 25 min. There was an exotherm and the oil bath was removed. The reaction mixture foamed badly. The oil bath was slowly replaced and reaction was continued for 1.5 hr after the addition was complete until the foaming stopped. A little of the mixture was lost out the condenser. The mixture was allowed to cool to ca. 110 ° C. and then poured onto 1.2 kg of ice. The product was collected, washed with water and dried in the oven to give 28.76 g (88%), melting point 224°–228° C. (trace of fast spot on thin layer chromatography.) Re-crystallization from 700 ml of water gave 23.66 g (72%) of product, melting point 233°–237° C. (thin layer chromatography 10% MeOH/CH$_2$Cl$_2$ single spot).

EXAMPLE 4—7-Hydroxy-1,2,3,4-tetrahydroquinoline

To a suspension of 9.79 g (60 mmol) of 7-hydroxy-3,4-dihydrocarbostyril in 40 ml of toluene in a 250 ml 3-necked flask provided with magnetic stirrer, condenser with nitrogen connection and a rubber septum was added 60 ml of 2M boranemethylsulfide complex in toluene. A heating mantle was put on. In 15 min the mixture was foaming badly, its temperature was 90°, and material was going out the condenser. The mantle was removed. After 10 min it was replaced with less heat. After 20 min the internal temperature was 90° C. and the mixture was foaming. It was then held at 90°–104° C. for 1 hr 50 min. At 1 hr 30 min thin layer chromatography showed that no starting material was present. To this was added 25 ml of methanol dropwise during 20 min. It was reconcentrated in vacuo. The residue was treated with methanol and reconcentrated twice. The 12 g of residue was crystallized from water to give 8.19 g (91%) of crude product, melting point 87°–91° C., with foaming.

EXAMPLE 5—7-Hydroxy-1,2,3,4-tetrahydroquinoline

To a suspension of 9.79 g (60 mmol) of 7-hydroxy-3,4-dihydrocarbostyril in 40 ml of toluene in a 250 ml 3-necked flask provided with magnetic stirrer, condenser with nitrogen connection and a rubber septum was added 60 ml of 2M boranemethylsulfide complex in toluene. A heating mantle was put on. The temperature was raised during 20 min to 85° C. An exotherm occurred and the mantle was temporarily removed. The temperature was then held at ca. 100° C. for 3 hr. The reaction was cooled and some flocculent material was filtered off. The filtrate was concentrated in vacuo, allowed to stand overnight and then reconcentrated with methanol to 8.76 g of dark oil. It did not crystalize with hexane so it was dissolved in 25 ml of methanol and 6.96 g of maleic acid was added. The acid dissolved and the maleate complex crystallized out. The complex was filtered off after cooling overnight in the refrigerator to give 8.096 g (51%) of maleate, melting point 141°–143° C. The filtrate was concentrated in vacuo to 8.49 g of brown oil. The oil was cooled overnight in the refrigerator with 10 ml of acetonitrile. The solid formed was collected to give 2.17 g (14%) of maleate, melting point 137–°140° C. The two crops were combined.

B. Tetrahydroquinoline Nitration Method

Chart 2 shows the preparation of 7-hydroxy-1,2,3,4-tetrahydroquinoline from tetrahydroquinoline. The first two steps from 5 to 6 and from 6 to 7 are generally described in the literature. See, M. Kulka, R.H.F. Manske, "The Nitration of Some Quinoline derivatives," Can.J.Chem. 1952, 30, 720, and J.v. Braun, A. Grabowski, M. Rawicz, Ber. 1913, 46, 3169, respectively. Nitration of 5 occurs mainly in the 7-position to give 6 as shown. The crude yield of nitroquinolines is close to quantitative, but after recrystallization about 50% of the 7-isomer 6 is obtained in a fairly pure state.

Hydrazine catalyzed with Raney nickel reduces the nitro group to an amino group quantitatively. The amine 7 is quite sensitive to air.

The amino group can be hydrolyzed to give 7-hydroxy-1,2,3,4-tetrahydroquinoline in the presence of a strong aqueous acid and at a temperature of from about 140° to 180° C. A preferred temperature is 165°±5° C. The reaction can occur at atmospheric pressure. In a preferred embodiment, the amino group is hydrolyzed off with strong aqueous acid such as phosphoric, sulfuric, methanesulfonic, trifluoromethanesulfonic, and hydrobromic acids at a temperature from about 140° C. to 180° C., under atmospheric or higher pressure. 7-Hydroxy-1,2,3,4-tetrahydroquinoline 4 is obtained in 70% yield after recrystallization.

CHART 2

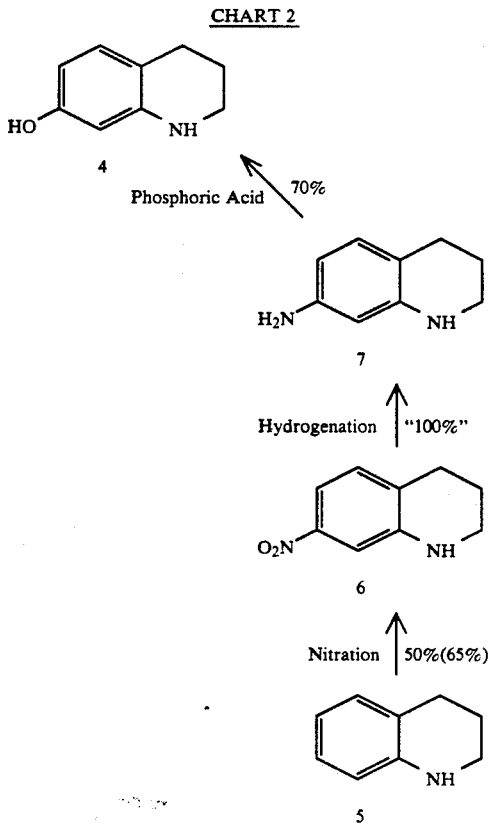

EXAMPLE 6—7-Nitro-1,2,3,4-tetrahydroquinoline

To 75 ml of 96.6% sulfuric acid cooled in a salt-ice bath was added dropwise 25 ml (0.2 mol) of 2,3,4-tetrahydroquinoline. After 30 min concomitant addition of 9.5 ml (0.2 mol) of 90% nitric acid in 40 ml of sulfuric acid was started at such a rate that the temperature remained at 5°-10° C. The addition of the quinoline was finished in 50 min. The addition of the nitric acid was finished in 30 min. The tetrahydroquinoline forms lumps which are slow to dissolve. The reaction mixture was stirred in the ice bath for 3 hr and then poured onto 1.4 kg of ice. The solution was neutralized to pH.8 with 255 g of sodium carbonate. The precipitate was collected, washed with water and allowed to stand in the hood overnight to give 44 g of crude product. This material was combined with 36 g from a similar experiment and recrystallized from ca. 200 ml of methanol to give 35 g (49%) of dark orange solid, melting point 60°-63° C. compared to literature reports of 62°-63° C.

EXAMPLE 7—7-Amino-1,2,3,4-tetrahydroquinoline

A 1 l round-bottomed flask fitted with thermometer, magnetic stirrer, addition funnel, and condenser with nitrogen inlet was charged under nitrogen with 26.73 g (0.15 mol) of 7-nitro-1,2,3,4-tetrahydroquinoline 6, 150 ml of methanol and 3.7 g of Raney nickel slurry rinsed with methanol. Addition of a solution of 16.5 ml (0.33 mol) of hydrazine hydrate in 15 ml of methanol to the stirred mixture was started. The reaction mixture was warmed to start the reaction after about one-third of the hydrazine solution had been added. Addition of the hydrazine took 45 min. Then the reaction mixture was heated under reflux to complete the reduction. The catalyst was filtered off through Celite and washed with methanol. The filtrate was concentrated in vacuo and reconcentrated twice with toluene to remove water. The residue was crystallized from hexane to give 21.92 g of product as a black solid.

EXAMPLE 8—7-Hydroxy-1,2,3,4-tetrahydroquinoline

A 300 ml Parr bomb was charged with 120 g of 70% phosphoric acid and 12 g. (81 mmol) of 7-amino-1,2,3,4-tetrahydroquinoline 7. It was stirred and heated at 160° C. for 20 hours. A pressure of ca. 55 lb developed. The cooled contents were rinsed into a 600 ml beaker with 150 ml of water and neutralized to pH 6 with 64 g of sodium carbonate. The precipitate was collected, rinsed with water and dried to give 11.88 g (98%) of crude product, melting point 83°-87° C. Recrystallization from 50 ml of toluene with 1 g of charcoal gave 8.36 g (69%) of tan solid, melting point 90°-92° C. Material which has been purified by filtration through silica gel has a melting point range of 90°-96° C.

While this embodiment has been described with respect to constant volume conditions and the use of phosphoric acid, it will be apparent to those skilled in the art that the reaction can be conducted in other strong aqueous acids, under ambient pressure conditions at temperatures between 140° to 180° C. The strong aqueous acid can be selected from the group consisting of phosphoric, sulfuric, methanesulfonic, trifluoromethane sulfonic, hydrobromic acids, and mixtures thereof.

II. Syntheses of Laser Dyes Utilizing 7-Hydroxy-1,2,3,4-Tetrahydroquinoline

A Laser Dye 1,11-Bis(2,2,2-trifluoroethyl)-1,2,3,4,8,9,10,11-octahydro-6-(2-methoxycarbonylphenyl)-dipyrido[3,2-b:2',3'-i]xanthylium perchlorate The efficient synthesis of 7-hydroxy-1,2,3,4-tetrahydroquinoline enables the synthesis of a laser dye having the following structure:

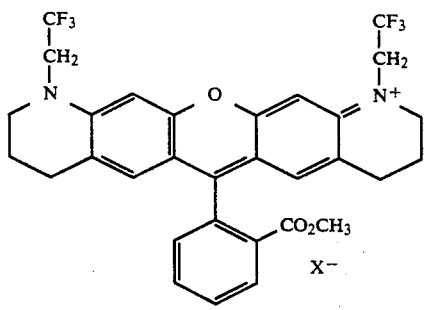

The aminophenol precursor to this dye was made by alkylation of 7-hydroxy-1,2,3,4-tetrahydroquinoline. Trifluoroethyl tosylate was the alkylating agent for preparing 1-trifluoroethyl-1,2,3,4-tetrahydro-7-hyroxyquinoline, which was converted with phthalic anhydride to the rhodamine 1,11-bis(2,2,2-trifluoroethyl)-1,2,3,4,8,9,10,11-octahydro-6-(2-carboxyphenyl)-dipyrido[3,2-b:2',3'-i]xanthylium perchlorate in 85% phosphoric acid at 170° C. (structure 8), which in turn was converted to the methyl ester (structure 9).

CHART 3

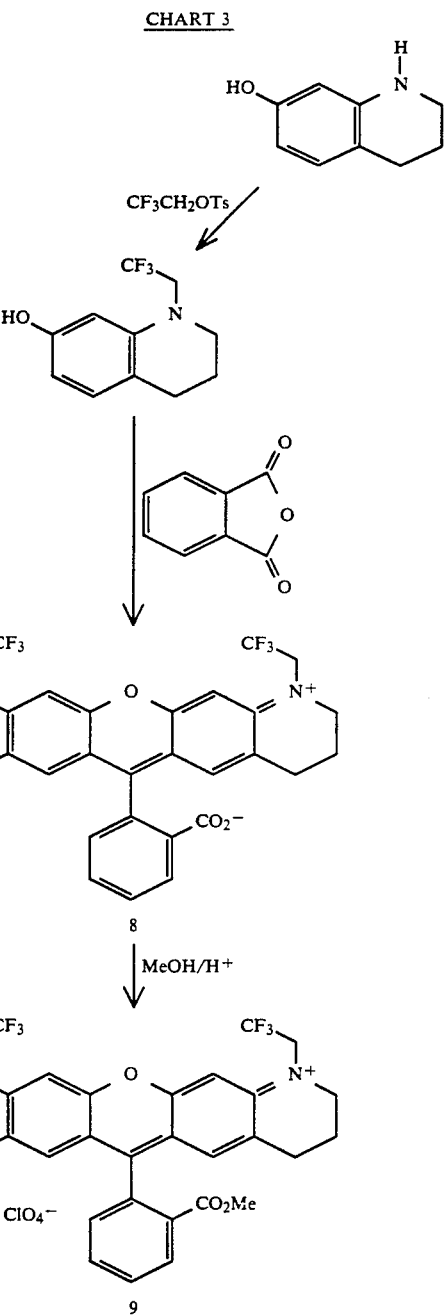

EXAMPLE 9—Purification of 7-hydroxy-1,2,3,4-tetrahydroquinoline

A mixture of 80 g of crude 7-hydroxy-1,2,3,4-tetrahydroquinoline and 300 ml of methylene chloride was filtered to remove a fine precipitate. The filtrate was chromatographed on 800 ml of silica gel in methylene chloride. Elution was with methylene chloride containing increasing amounts of ethyl acetate. Those fractions eluted with 10-15% of ethyl acetate were concentrated to give 38 g of pure material (thin layer chromatography 50% ethyl acetate/hexane on silica gel). There was about 19 g of fairly impure material in fractions before and after these fractions.

EXAMPLE 10—Alkylation of 7-hydroxy-1,2,3,4-tetrahydroquinoline with trifluoroethyl tosylate A mixture of 24 g (0.16 mol) of 7-hydroxy-1,2,3,4-tetrahydroquinoline, and 50 g (0.197 mol) of 2,2,2-trifluoroethyl p-toluenesulfonate was stirred under nitrogen in an oil bath at 180°-190° C. for four hours. The cooled mixture was partitioned between 200 ml of methylene chloride and 200 ml of water. The aqueous phase was adjusted to pH 7 by the addition of solid sodium carbonate. The organic phase was separated. The aqueous phase which contained solid was washed with 100 ml of methylene chloride. The organic phases were combined, washed with 100 ml of water and dried over sodium sulfate. Some black tar separated. The mixture was filtered and concentrated in vacuo to leave 64.83 g of dark oil. This was dissolved in methylene chloride and filtered through 400 ml of silica gel in a 600 ml coarse sintered glass funnel. Fractions of 200 ml were collected. The first two contained 33 g of unreacted tosylate. The next five contained 11.34 g (31%, more typically 20%) of product as a pink solid. Ethyl acetate (400 ml) eluted 5.23 of dark oil which thin layer chromatography showed to contain some unreacted tetra-hydroqinoline. An analytical sample of the product was prepared by recrystallization from hexane with charcoal to give long white needles, melting point 106°-108° C. Analysis calculated for $C_{11}H_{12}F_3NO$: C,57.14; H, 5.23; N, 6.06. Found: C, 56.99; H, 5.18; N, 602.

EXAMPLE 11—Synthesis of 1,11-bis(2,2,2-trifluoroethyl)-1,2,3,4,8,9,10,11-octahydro-6-(2-carboxyphenyl)-dipyrido[3,2-b:2',3'-i]xanthyliumhydroxyde, inner salt (rhodamine structure 8)

A mixture of 9.25 g (40 mmol) of 1-(2,2,2-trifluoroethyl)-1,2,3,4-tetrahydro-7-hydroxyquinoline and 8.89 g (60 mmol) of phthalic anhydride in a 250 ml round bottom flask was stirred and heated in an oil bath at 170° C. under nitrogen for 3 hours. The mixture gradually thickened. It was then removed from the bath and allowed to cool slightly. To it Was added 9.25 g (40 mmol) of 1-(2,2,2-trifluoroethyl)-1,2,3,4-tetrahydro-7-hydroxyquinoline and 30 ml of 85% phosphoric acid. It was then heated in the 170°-173° C. oil bath for 4.5 hrs. It was again allowed to cool slightly and 70 ml of methanol was added dropwise to the hot reaction mixture. It was allowed to reflux for 5 minutes and then transferred to an Erlenmeyer flask. To it was added with stirring 200 ml of water in portions. A red-gold solid precipitated. The mixture was cooled in the refrigerator overnight. The solid was collected, washed with water (two 10 ml portions) and dried four hours at water pump vacuum at 100° C. to give 25.93 g of brownish solid.

EXAMPLE 12-Esterification of 1,11-bis(2,2,2-trifluoroethyl)-1,2,3,4,8,9,10,11-octahydro-6-(2-carboxyphenyl)-dipyrido[3,2-b:2',3'-i]xanthyliumhydroxide, inner salt to form 1,11-bis(2,2,2-trifluoroethyl)-1,2,3,4,8,9,10,11-octahydro-6-(2-methoxycarbonylphenyl)-dipyrido[3,2-b:2',3'-i]xanmthylium perchlorate (rhodamine structure 9)

To 4 g (6 mmol) of the rhodamine 8 dissolved in 50 ml of methanol was added carefully 4 ml of trifluoromethanesulfonic acid. The mixture was stirred and heated under reflux in a nitrogen atmosphere for 48 hours. It was concentrated in vacuo to about 13.5 g and the residue was treated with 35 ml of saturated sodium bicarbonate solution in portions until the pH was about 6. A gum separated out. This gum gradually solidified on scratching with the addition of a little ethyl acetate. The red solid that formed was collected and allowed to dry overnight to give 4.35 g of crude triflate.

To a solution of this triflate in 25 ml of methanol was added 1 ml of 70% perchloric acid. This mixture was seeded, scratched and cooled in the refrigerator for one hour. The solid was collected, rinsed with 50% aqueous methanol and air-dried overnight to give 3.09 g (76%) of crude perchlorate. For analysis this material was recrystallized four times form 50% aqueous methanol to give red prisms with a green sheen, melting point 254°–257° C. Analysis calculated for $C_{31}H_{27}ClF_6N_2O_7$: C, 54.04; H, 3.95; N, 4.07. Found: C, 54.10; H, 3.98; N, 4.01.

B. Laser Dye 1,11-Bis(3,3,3-trifluoropropyl)-1,2,3,4,8,9,10,11-octahydro-6-(2-methoxycarbonylphenyl)-dipyrido[3,2-b:2',3'-i]xanthylium trifluoromethanesulfonate The efficient synthesis of 7-hydroxy-1,2,3,4-tetrahydroquinoline enables the synthesis of a laser dye having the following structure.

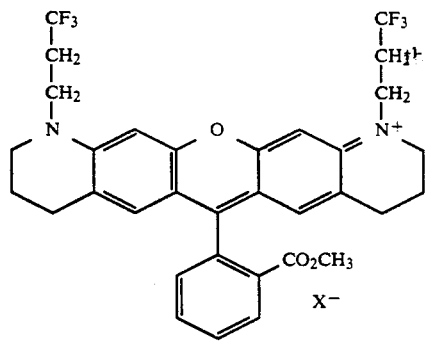

1-Trifluoropropyl-1,2,3,4-tetrahydroquinoline was made from trifluorochloropropane and the 7-hydroxy-1,2,3,4-tetrahydroquinoline in aqueous sodium acetate in a stirred pressure reactor at about 150° C. and 200psi. In this case, the rhodamine 1,11-bis(3,3,3-trifluoropropyl)-1,2,3,4,8,9,10,11-octahydro-6-(2-carboxyphenyl)-dipyrido[3,2-b:2',3'-i]xanthylium trifluoromethanesulfonate (rhodamine structure 10) was prepared in refluxing o-dichlorobenzene separating the water generated in the reaction by a trap and in turn was converted to the methyl ester (rhodamine structure 11).

CHART 4

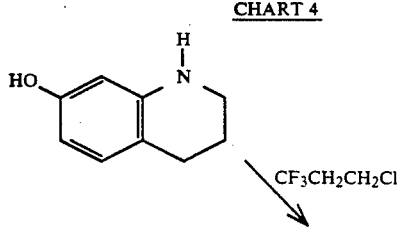

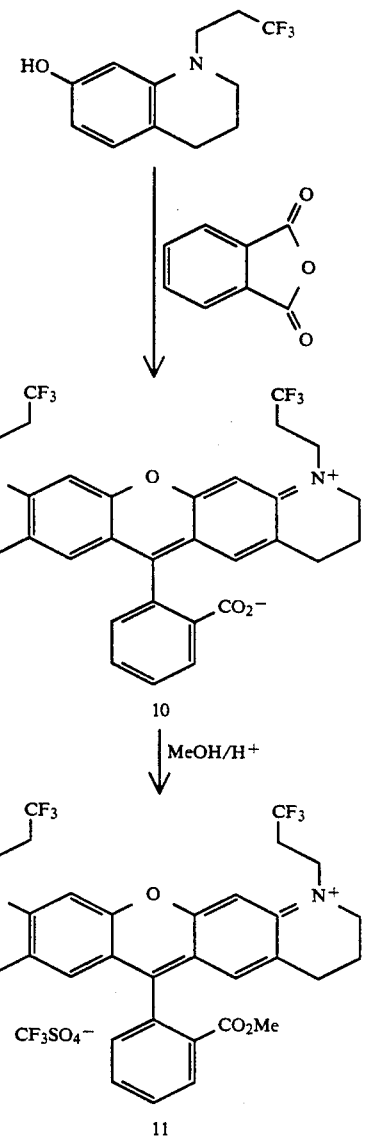

EXAMPLE 13—Alkylation of 7-hydroxy-1,2,3,4-tetrahydroquinoline with trifluorochloropropane A mixture of 7-hydroxy-1,2,3,4-tetrahydroquinoline 22.4 g (0.15 mol), anhydrous sodium acetate 18.4 g (0.225 mol), water 112 ml and trifluorochloropropane 29.8 g (22.8 ml, 0.225 mol) were placed in a Parr 300 ml pressure reactor. The reactor was cooled to 5° C., stirred, purged with nitrogen for six minutes and closed. It was stirred rapidly and heated to 150° C.(±5° C.) for 18 hours when the pressure dropped from 202 psi to 76 psi. It was allowed to cool to room temperature, whilst stirring, then to 5° C. and the excess pressure was released. It was warmed to 40° C., the reactor opened, and the mixture was poured into a 500 ml separatory funnel and was washed in with toluene (100 ml plus 30 ml). A pale orange heavy oil was extracted into the toluene whereas the rejected aqueous phase had a pH of 4 to 5. It was washed with 10% aqueous sodium carbonate, water, dried (sodium sulfate), filtered, evaporated to dryness and then on a vacuum pump at 3 mm at room temperature for three hours. 27.3 g (74% crude yield) of a brown gum was obtained that crystallized after standing two days in a 5° C. refrigerator under a nitrogen atmosphere. Thin layer chromatography on silica, developing with ethyl acetate/n-hexane (1:1, v:v), showed mainly the required product $R_f$ 0.75 and starting material (5 to 10%) $R_f$ 0.30.

This material was used directly in the next dye preparation step. It could be recrystallized from n-hexane but was still contaminated with the 7-hydroxy-1,2,3,4-tetrahydroquinoline starting material. For purification 9.2 g was chromatographed on a Woelm silica column (160 ml of silica powder), eluting with dichloromethane. The first 200 ml coming off just before a yellow ring, contained two faster running impurities on the ethyl acetate/n-hexane thin-layer detection chromatogram, and was rejected. The next four 50 ml samples, on evaporation gave 3.3 g, 1.5 g, 0.6 g and 0.2 g respectively of light-brown clear gum, which crystallized overnight and which was collected as product. 0.8 g was further purified by recrystallization from 150 ml of n-hexane to give pale-brown, translucent plates, melting point 72.5°-73.0° C.

Analysis calculated for $C_{12}H_{14}F_3NO$: C, 58.77; H, 5.75; N, 5.71. Found: C, 59.18; H, 5.83; N, 5.70%.

EXAMPLE 14—Synthesis of 1,11-bis(3,3,3-trifluoropropyl)-1,2,3,4,8,9,10,11-octahydro-6-(2-carboxyphenyl)-dipyrido[3,2-b:2',3'-i]xanthylium hydroxide, inner salt (rhodamine structure 10)

1-Trifluoropropyl-1,2,3,4-tetrahydro-7-hydroxyquinoline 27.2 g (0.11 mol) was dissolved and washed into a 250 ml, round-bottomed, single-neck flask with o-dichlorobenzene (50 ml+33 ml). Phthalic anhydride 12.3 g (0.083 mol, 1.5 mole equivalents to 2 mole equivalents of the base), two pieces of bumping stone and a magnetic stirring bead were added. The mixture was stirred and brought to reflux when some frothing occurred and the deep red color of the rhodamine appeared. The refluxing was continued for 3.5 hr and 2.0 ml of water from the reaction was collected in a trap. The mixture was allowed to cool whilst stirring when some dye precipitated, and the flask was stored at 5° C. for two days. A fine solid was filtered off and sucked dry (18.2 g wet weight), which was stirred and boiled with 10% sodium hydroxide 200 ml for half an hour, and the suspension was allowed to cool. Filtration in a wide-necked funnel gave a deep red-brown solid and a light orange filtrate. After the solid was washed with water, the filtration was slow and the filtrate was deep red. The water washing was continued until the filtrate was colorless, when the solid was sucked dry and was dried several days in the fume hood, the solid yielded 13.6 g (41%). This was analyzed directly as a zwitterion, melting point 300° C., decomp.

Analysis calculated for $C_{32}H_{28}F_6N_2O_3$: C, 63.78; H, 4.68; N, 4.65. Found for a sample dried at 60° C. at 1 mm for two hours: C, 63.90, H, 4.68; N, 4.57%.

The material was sparingly soluble in methanol giving a red solution and orange-red fluorescence, and would not dissolve sufficiently in methanol, water, ethanol or their mixtures to permit convenient recrystallization. Thin layer chromatography on alumina gave a single, strongly fluorescent spot, $R_f$ 0.2 eluting with isopropanol, or $R_f$ 0.8 eluting with methanol. A careful comparison with the rhodamine dye obtained directly from 7-hydroxy-1,2,3,4-tetrahydroquinoline showed no contamination. The yield of the above reaction varied up to 45%, whereas using the chromatographed base and 2 mole equivalents of phthalic anhydride with two mole equivalents of the base increased it to 66%.

EXAMPLE 15—Esterification of 1,11-bis(3,3,3-trifluoropropyl)-1,2,3,4,8,9,10,11-octahydro-6-(2-carboxyphenyl)-dipyrido[3,2-b:2',3'-i]xanthylium hydroxide, inner salt to form 1,11-bis(3,3,3-trifluoropropyl)-1,2,3,4,8,9,10,11-octahydro-6-(2-methoxycarbonylphenyl)-dipyrido[3,2-b:2',3'-i]xanthylium trifluoromethanesulfonate (rhodamine structure 11)

A 3% (v/v) solution of trifluoromethanesulfonic acid in anhydrous methanol was made by dripping 10 ml of anhydrous acid into 330 ml with stirring over five minutes. The rhodamine 10, 20.1 g (0.03 mol), was transferred and washed into a 250 ml round-bottomed, three necked flask fitted with stirrer and an efficient reflux condenser having a loose cotton-wool plug by means of 167 ml of the trifluoromethanesulfonic acid solution (66% excess). The mixture was refluxed and stirred for 94 hours and the esterfication was monitored by thin-layer chromatography on fresh alumina eluting with methanol-rhodamine 10 Rf 0.85, rhodamine 11 Rf 0.7. Warm (60° C.) water 42 ml was added steadily to the stirred mixture which was brought to reflux and stirred for 7 minutes before filtering hot. On cooling crystals of the 1,11-bis(3,3,3-trifluoropropyl)-1,2,3,4,8,9,10,11-octahydro-6-(2-methoxycarbonylphenyl)-dipyrido[3,2-b:2',3'-i]xanthylium trifluoromethanesulfonate appeared and the flask was stored at 5° C. overni     . The material was filtered off, was washed twice with cold methanol/water (1:1, v:v), was sucked dry and was dried in the hood for three days—22.1 g (86%). Recrystallization of 5 g from 100 ml of methanol/water (2:1, v:v) gave 4.2 g of dark green needles with golden metallic sheen, mp. 236.5°-237° C.

Analysis calculated for $C_{34}H_{31}F_9N_2O_6S$: C, 53.26; H, 4.08; N, 3.65; S, 4.18. Found: C, 53.64; H, 4.06; N, 3.69; S, 4.23.

We claim:

1. A method of making 7-hydroxyl-1,2,3,4-tetrahydroquinoline which comprises the steps of:
   a) nitrating 1,2,3,4-tetrahydroquinoline in the presence of sulfuric acid and nitric acid to obtain 7-nitro-1,2,3,4-tetrahydroquinoline;
   b) isolating 7-nitro-1,2,3,4-tetrahydroquinoline;
   c) reducing 7-nitro-1,2,3,4-tetrahydroquinoline in the presence of Raney nickel and hydrazine to obtain 7-amino-1,2,3,4-tetrahydroquinoline;
   d) isolating 7-amino-1,2,3,4-tetrahydroquinoline; and
   e) hydrolyzing 7-amino-1,2,3,4-tetrahydroquinoline with a strong aqueous acid selected from the group consisting of phosphoric, sulfuric, methanesulfonic, trifluoromethanesulfonic hydrobromic acids and mixtures thereof and at a temperature from about 140° C. to 180° C. and a pressure of less than about 55 psi to obtain 7-hydroxy-1,2,3,4-tetrahydroquinoline.

2. The method of claim 1 wherein said strong aqueous acid is 70% phosphoric acid and step e) occurs at above atmospheric pressure.

3. The method of claim 1 wherein said strong aqueous acid is 85% phosphoric acid and step e) occurs at above atmospheric pressure.

* * * * *